United States Patent [19]
Furnish et al.

[11] Patent Number: 6,071,235
[45] Date of Patent: Jun. 6, 2000

[54] CORONARY STABILIZING RETRACTOR WITH OCCLUDING MEANS

[75] Inventors: Gregory R. Furnish, Louisville, Ky.; Christopher S. Looney, Roswell, Ga.

[73] Assignee: Genzyme Corporation, Cambridge, Mass.

[21] Appl. No.: 08/899,836

[22] Filed: Jul. 24, 1997

Related U.S. Application Data

[63] Continuation-in-part of application No. 08/794,226, Jan. 31, 1997, abandoned, which is a continuation-in-part of application No. 08/639,214, Apr. 26, 1996.

[51] Int. Cl.⁷ .................................. A61B 1/22; A61B 1/30
[52] U.S. Cl. ............................................. 600/235; 600/201
[58] Field of Search .................................... 600/201, 203, 600/210, 213, 214, 217, 776–778, 234, 235, 229; 606/1

[56] References Cited

U.S. PATENT DOCUMENTS

| | | | |
|---|---|---|---|
| 2,594,086 | 4/1952 | Smith | 600/228 |
| 2,693,795 | 11/1954 | Grieshaber | 600/213 |
| 2,863,444 | 12/1958 | Winsten | 600/214 |
| 3,409,013 | 11/1968 | Berry | 600/201 X |
| 3,882,855 | 5/1975 | Schulte et al. | 600/201 X |
| 3,943,592 | 3/1976 | Bhaskar et al. | 600/240 X |

(List continued on next page.)

FOREIGN PATENT DOCUMENTS

| | | | |
|---|---|---|---|
| 2216893 | 2/1999 | Canada . | |
| 630 629 | 12/1994 | European Pat. Off. . | |
| 668 058 | 8/1995 | European Pat. Off. . | |
| 1019217 | 10/1952 | France . | |
| 90 04 5130 | 6/1990 | Germany . | |
| 970751 | 8/1997 | Norway . | |
| 970752 | 8/1997 | Norway . | |
| 970753 | 8/1997 | Norway . | |
| 970754 | 8/1997 | Norway . | |
| 2233561 | 1/1991 | United Kingdom | 600/234 |

| | | |
|---|---|---|
| WO 87/04081 | 7/1987 | WIPO . |
| WO 94/14383 | 7/1994 | WIPO . |
| WO 95/17127 | 6/1995 | WIPO . |
| WO 97/10753 | 3/1997 | WIPO . |
| WO 98/27869 | 7/1998 | WIPO . |

OTHER PUBLICATIONS

Akiharu Eguchi, Heart Retractor for Use in Anatomosis in Coronary By–Pass Surgery, vol. 40 No. 1, 1987, Japanese Journal of Thoracic Surgery, p. 39.

"Self–Retaining Epicardial Retractor for Aortocoronary Bypass Surgery," Victor Parsonnet, MD, et al., *The Journal of Thoracic and Cardiovascular Surgery*, 629–30, 1979.

"A New Internal Mammary Artery Retractor," M. Bugge, *Thoracic Cardiovascular Surgeon* 38, 316–17 (1990).

(List continued on next page.)

*Primary Examiner*—Richard J. Apley
*Assistant Examiner*—Denise Pothier
*Attorney, Agent, or Firm*—Richard D. Allison; Thomas J. DesRosier

[57] ABSTRACT

An apparatus for stabilizing a predetermined area on a heart of a patient to enable a surgical procedure, the apparatus comprising a bifurcated member having two elongated prongs and an elongated handle segment attached to the bifurcated member. Selected portions of the apparatus can be constructed from a memory metal alloy, such as nitinol, to allow the surgeon to adapt the apparatus to a particular surgical procedure. The bifurcated member can be either fixably or pivotally attached to the handle segment. The apparatus may further comprise an attachment or inlay to prevent lateral movement thereof when being used in the surgical procedure. The apparatus may additionally include a cleat for securing a portion of the surgical thread used during the surgical process. Another aspect of the present invention is a member slidably attached to a portion of the handle segment that is movable between a position compressing an artery to reduce or stop blood flow and a position spaced apart from the artery.

7 Claims, 4 Drawing Sheets

U.S. PATENT DOCUMENTS

| | | | |
|---|---|---|---|
| 4,052,980 | 10/1977 | Grams et al. | 600/211 X |
| 4,457,300 | 7/1984 | Budde | 600/228 |
| 4,461,284 | 7/1984 | Fackler | 128/20 |
| 4,616,634 | 10/1986 | Garcia | 600/210 |
| 4,616,635 | 10/1986 | Caspar et al. | 600/215 |
| 4,617,738 | 10/1986 | Kopacz | 30/339 |
| 4,637,377 | 1/1987 | Loop | 128/1 |
| 4,726,356 | 2/1988 | Santilli et al. | 128/20 |
| 4,949,707 | 8/1990 | LeVahn et al. | 128/20 |
| 4,973,300 | 11/1990 | Wright | 600/37 |
| 5,133,724 | 7/1992 | Wilson, Jr. et al. | 606/151 |
| 5,167,223 | 12/1992 | Koros et al. | 600/211 X |
| 5,201,325 | 4/1993 | McEwen et al. | 600/202 X |
| 5,222,976 | 6/1993 | Yoon | 606/223 |
| 5,318,013 | 6/1994 | Wilk | 600/225 X |
| 5,337,736 | 8/1994 | Reddy | 600/217 |
| 5,339,801 | 8/1994 | Poloyko et al. | 128/20 |
| 5,391,147 | 2/1995 | Imran et al. | 604/95 |
| 5,429,118 | 7/1995 | Cole et al. | 600/121 |
| 5,449,374 | 9/1995 | Dunn et al. | 600/214 X |
| 5,498,256 | 3/1996 | Furnish | 606/1 |
| 5,509,890 | 4/1996 | Kazama | 600/37 |
| 5,518,503 | 5/1996 | Rooney et al. | 600/240 |
| 5,529,571 | 6/1996 | Daniel | 600/213 X |
| 5,558,621 | 9/1996 | Heil | 600/201 X |
| 5,782,746 | 7/1998 | Wright | 600/37 |
| 5,875,782 | 3/1999 | Ferrari et al. | 128/898 |
| 5,888,247 | 3/1999 | Benetti | 623/66 |
| 5,894,843 | 4/1999 | Benetti et al. | 128/898 |
| 5,957,835 | 9/1999 | Anderson et al. | 600/201 |

OTHER PUBLICATIONS

"A Simple, Inexpensive Method of Heart Retraction During Coronary Artery Bypass Surgery," G.D. Angelini, M M.Ch., F.R.C.S., *The Annals Thoracic Surgery* 46:246–47, Aug. 1988.

A New Device for Exposing the Circumflex Coronary Artery, Akio Matsuura, MD, et al., *The Annals of Thora Surgery* 1995; 59:1249–50.

"Correspondence and Brief Communications," *Archives of Surgery*, vol. 115, 1136–37, Sep. 1980.

"Internal Mammary Artery Dissection: A Three Dimensional Sternal Retractor," D. Roux, MD, et al., *Journa Cardiovasic Surgery*, 30, 996–97, 1989.

"Off–Bypass Coronary Bypass Grafting Via Mimithoracotomy Using Mechanical Epicardial Stabilization," Joche Cremer, MD, et al., *The Annals of Thoracic Surgery* 1997; 63:S79–83.

"Single Coronary Artery Grafting—A Comparison Between Minimally Invasive 'Off Pump' Techniques and Conventional Procedures," Johannes Bonatti, et al., *European Journal of Cardio–Thoracic Surgery*, 14 (Sup I) (1998) S7–S12.

"Less Invasive Coronary Surgery: Consensus From the Oxford Meeting," Stephen Westaby, FRCS, and Federico Benetti, MD, *The Annals of Thoracic Surgery* 1996; 62:924–31.

"Mini–Sternotomy for Coronary Artery Bypass Grafting," Kit V. Arom, MD, PhD, et al. *The Annals oif Thorac Surgery* 1996; 61:1271–2.

"Limited Access Myocardial Revascularization," Denton A. Cooley, MD, Texas Heart Institute Journal, vol. 23, No. 2, 1996.

"Mini–Sternotomy for Coronary Artery Bypass Grafting," *The Annals of Thoracic Surgery*, 1996; 62:1884–85.

"The Cardiac Rag—Simple Exposure of the Heart," Michael M. Bedellino, MD, et al., *Texas Heart Institute Journal*, vol. 15, No. 2, 1988, 134–35.

"Fabric Heart Retractor for Coronary Artery Bypass Operations," Shigeru Kazama, MD, et al., *The Annals of Thoracic Surgery* 1993; 55:1852–3.

"Minimally Invasive Coronary Artery Bypass Grafting," Antonio M. Calafiore, MD, et al., *The Annals of Thoracic Surgery*,1996; 62:1545–8.

"Improved Visualization of the Internal Mammary Artery With a New Retractor System," John Pittman, MD, et al., *The Annals of Thorac Surg*, 1989; 48:869–70.

"A Modified Sternal Refractor," Nelson Ancalmo, MD, and John L. Ochsner, MD, Aug. 8, 1975.

"A Versatile Retractor for Use in Harvesting the Internal Mammary Artery and Performing Standard Cardiac Operations," Steven J. Phillips, MD, and Marge Core, RN, *The Journal of Thoracic Surgery*, 1989; 97: 633–35.

"Surgical Management of Diseased Intracavitary Coronary Arteries," John L. Ochsner, MD and Noel L. Mills, M *The Annals of Thoracic Surgery*, vol. 38, No. 4, 356–62 (Oct. 1984).

"Technique of Internal Mammary—Coronary Artery Anastomosis," *The Journal of Cardiovascular Surgery*, 78:45 79, 1979.

"Graduated Probes for Coronary Bypass Surgery," George E. Green, MD, *The Journal of Thoracic and Cardiovascular Surgery*, vol. 68, No. 3, 424–27 (Sep. 1974).

"A Modified Sternal Retractor for Exposure of the Internal Mammary Artery," Peter P. McKeown, MB,BS, et al *The Society of Thoracic Surgeons*, 1980.

"A New Concept in Sternal Retraction: Applications for Internal Mammary Artery Dissection and Valve Replacement Surgery," Aurelio Chaux, MD, and Carlos Blanche, MD, *The Annals of Thoracic Surgery*, 473–74, Oct. 1986.

The Japanese Journal of Thoracic Surgery, 1989, vol. 42, No. 2 (translation of summary included).

"Heart Retractor," Japanese article (undated) (translation of summary included).

"Tecnica Operatoria," Minerva Cardioangiologica, vol. 23—N. 6–7 (1975) (translation of summary included).

"Microsurgery: The New Frontier," V. Mueller, 1968.

"Neurosurgical Instruments," V. Mueller, Untitled Medical Device Catalog, I17–I18, 1988.

"Heart Retractor for Use in Anastomosis in Coronary Artery By–Pass Surgery," *Japanese Journal of Thoracic Surgery*, vol. 40 No. 1, 1987 (translation of summary included).

"Triple Coronary Artery Revascularization on the Stabilized Beating Heart: Initial Experience," Raymond Cartier, MD, et al., *CJS*, vol. 41, No. 4, 283–288, Aug. 1998.

"Cardiac Retractor for Coronary Bypass Operations," John A. Rousou, MD, et al., *The Annals of Thoracic Surgery*, 1991, 52: 877–78.

"A New Retractor to Aid in Coronary Artery Surgery," A.J. DelRossi, MD, G.M. Lemole, MD, *The Annals of Thoracic Surgery*, vol. 36, No. 1, 101–02, Jul. 1983.

"New Helper Instrument in Cardiac Surgery," D. Roux, MD, et al., *The Annals of Thoracic Surgery*, 1989, 48: 595–6.

"Aortic Spoon–Jaw Clamp for Aorta–Saphenous Vein Anastomosis," Francis Robicsek, M.D., *Journal of Cardiac Surgery*, 1995; 10:583–585.

"Technique of Dissecting the Internal Mammary After Using the Moussali Bar," R.I. Hasan, et al. *European Journal of Cardiothoracic Surgery*,4:571–572, 1990.

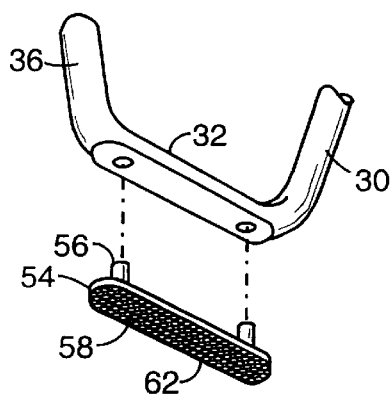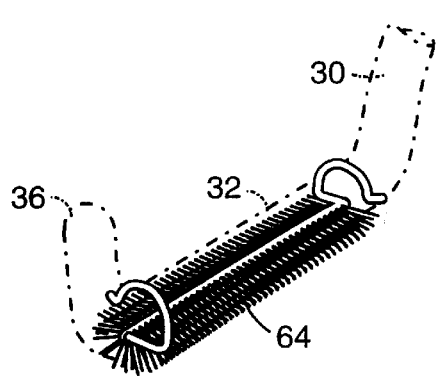
FIG. 4                    FIG. 5
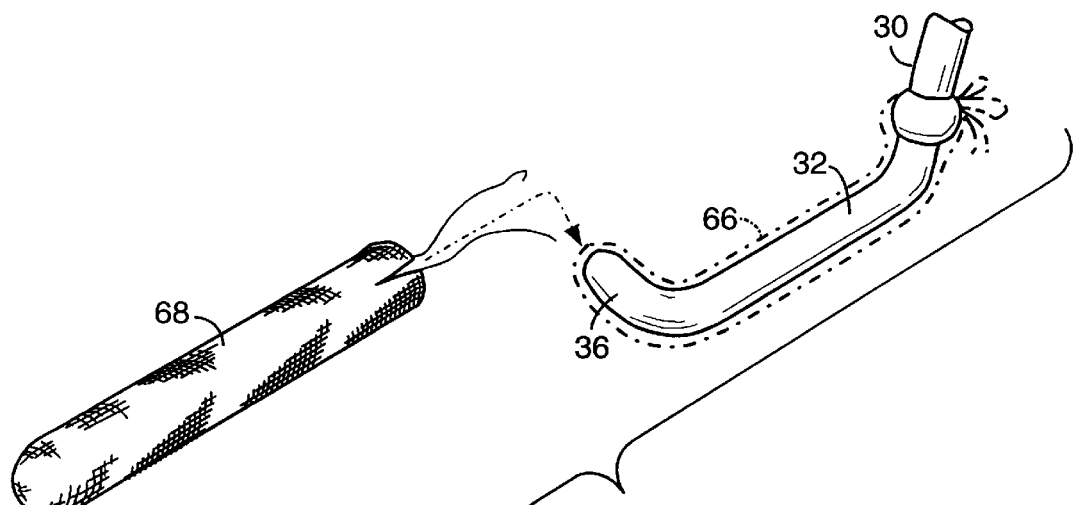
FIG. 6
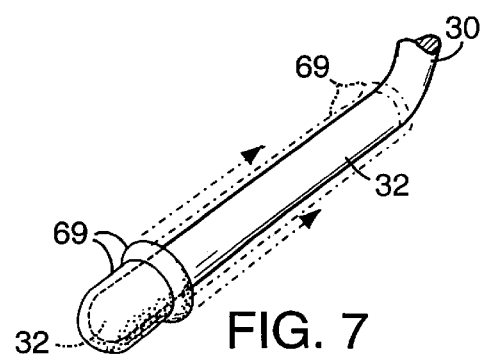
FIG. 7

CORONARY STABILIZING RETRACTOR WITH OCCLUDING MEANS

This application is a continuation-in-part of U.S. Ser. No. 08/794,226, filed on Jan. 31, 1997, which is pending, which is a continuation-in-part of U.S. Ser. No. 08/639,214, filed on Apr. 26, 1996, which is also pending.

BACKGROUND OF THE INVENTION

1. Field of the Invention

This invention relates to an apparatus for stabilizing a predetermined site of a patient's body during surgical intervention that better enables a surgeon to perform a surgical procedure at the site. In particular, the invention relates to an improved apparatus for stabilizing an area of the heart for performing minimally invasive coronary artery bypass grafting, in which the apparatus also includes an occluding means to occlude the coronary artery.

2. Background Art

Atherosclerosis or coronary artery disease is among the most common and serious health problems confronting the medical profession. In the past, many different approaches at therapy have been utilized. Surgical correction of occluded or stenosed coronary arteries via bypass grafting through conventional approaches, such as the stenotomy, are probably still the most common procedure performed today, especially where multiple bypass grafts are needed.

However, interventional techniques, such as percutaneous transluminal angioplasty (PTCA), have gained popularity as the method of choice for therapy of atherosclerotic occlusions for several reasons. The transluminal approach is a minimally invasive technique which subjects the patient to less trauma and less recovery time, especially when compared to bypass grafts which utilize homologous tissue, such as saphenous vein grafts. Often the patient suffers complications at the graft donor site which are worse than the sternotomy and anastomosis.

Although PTCA procedures are often successful, complications such as restenosis or thrombosis and embolism can occur. Intravascular stents are sometimes deployed at the PTCA site to lessen the occurrence of restenosis. However, restenosed vessels often require surgical intervention for correction.

Surgical correction of restenosis, as well as conventional bypass graft surgery, requires that the heart be stopped and the patient placed on a heart/lung bypass machine during the procedure. This occurs at considerable expense and risk to the patient. In an effort to reduce the expense, risk and trauma to the patient, physicians have recently turned to minimally invasive surgical approaches to the heart, such as intercostal and endoscopic access to the surgical site. In addition, utilization of alternative graft vessels, such as the internal mammary artery (IMA), have also greatly reduced the trauma to the patient and increased the efficacy of surgical therapy.

Prior to the present invention, however, attempts at performing minimally invasive bypass grafting on a beating heart were thought to be too tedious, dangerous and difficult because of the delicate nature of the surgical procedure, the lack of adequate access through a reduced surgical field, and the lack of a way to adequately stabilize and reduce movement at the graft site. Such a minimally invasive bypass grafting performed on the beating heart eliminates the expense and risk of stopping the heart and the necessity of the heart lung bypass machine and decreases patient recovery time. For single or double bypass procedures, especially where the IMA is utilized, patient trauma and recovery time is even further decreased.

SUMMARY OF THE INVENTION

The above problems of the prior art are overcome by the present invention, which provides an apparatus for stabilizing a predetermined area on a heart or other organ of a patient to enable a surgical procedure to be performed. The apparatus of the present invention comprises a bifurcated member having two prongs, an elongated handle segment, and a means for joining the handle segment to the bifurcated member. Each prong of the bifurcated member, also known as a tine assembly, has a first section, a second section, and preferably a third section. The first section is adjacent the handle segment and connects the handle segment to the second section. The second section engages the heart or other organ where the surgical procedure occurs and terminates in the third section. The third section can be used as a tissue retractor. Selected portions of the apparatus can be constructed from a memory metal alloy, such as nitinol, to allow the surge on to adapt the apparatus to a particular surgical procedure.

Since the second section engages the heart or other organ, it is desired that the section further comprises a means to prevent sliding. The present invention can employ many different stabilizing means, including, for example, a textured portion on at least a portion of one second section, an insert disposed on the second section having a plurality of teeth, an insert having a plurality of flexible hooks, an insert having a plurality of bristles, or even a flexible covering disposed over at least a portion of the second section. The flexible covering can be a cloth, such as cotton, or a tubular member formed from a material such as silicon.

One aspect of the present invention is that it can include a means on the apparatus for occluding an artery. The occluding means preferably is movably or slidably coupled to either a portion of the bifurcated member or a portion of the handle segment. The preferred embodiment of the occluding means comprises an elongated occluding member having an engaging end adapted to at least partially compress a portion of the artery and defines an elongated slot through a portion of its length into which a portion of a fastener is disposed. The occluding member is slidably movable between an engaged position to compress the artery and a released position. Rotation of the fastener moves the occluding means between a locked and unlocked position, depending on the direction of rotation of the fastener. In the locked, or tightened, position, the fastener frictionally holds the occluding member and, in the unlocked position, the occluding member and the fastener are spaced apart so that the occluding member is slidably movable. The occluding means preferably further comprises a guide member so that, in conjunction with the fastener also disposed within the slot, the occluding member can only slide linearly.

Another aspect of the present invention is that it can include a means for rotatably and pivotally connecting the bifurcated member to the handle segment, preferably using a ball and socket design. In conjunction, the present invention comprises a means for locking the bifurcated member in a desired position relative to the handle segment when the bifurcated member is disposed on the heart of a patient. The surgeon tightens the ball and socket to frictionally hold the assembly using a tightener located at the upper end of the handle segment, which is advantageous during a surgical procedure in which space within the surgical site is limited.

A further aspect of the present invention is that it comprises a means for securing a portion of a surgical thread used during the surgical procedure. In the preferred embodiment, the securing means comprises at least one cleat disposed on the apparatus. The cleat or cleats can be disposed at the end of the third section of each of the prongs of the bifurcated member, another portion of the bifurcated member, or the handle segment. A cleat can also be disposed on the guide member of the occluding means.

The present invention can also encompass a means for movably mounting the handle segment to a rib retractor or other surgical device. The mounting means, which is preferably a swivel head assembly, holds the bifurcated member at the predetermined site, thus freeing a person from manually holding it.

As one skilled in the art will also appreciate, the apparatus of the present invention can be used in surgical procedures other than heart surgery, including, for example, soft tissue procedures such as vascular thrombosis repair, intestinal resection and anastomosis, other intra-abdominal procedures, and the like. Thus, it is an object of the invention to provide an apparatus for stabilizing a predetermined area of the heart or other organ of a patient to enable a surgeon to perform a surgical procedure.

In conjunction with stabilizing a predetermined area of a beating heart to enable a surgeon to perform a surgical procedure, another object of the present invention is to provide an occluding means to block, at least partially, an artery or vein to facilitate performance of the surgical procedure.

Another object of the invention is to provide an apparatus having selected portions constructed from a memory metal alloy, such as nitinol, to allow the surgeon to adapt the apparatus to particular surgical procedure and size constraints.

Yet another objective of the present invention is to provide an apparatus in which the bifurcated member can both rotate and/or pivot relative to the handle segment to ensure the maximum adaptability for work at the surgical site.

A further object of the invention is to provide an apparatus that also functions as a tissue retractor to assist the surgeon in accessing the surgical site.

Still another object of the invention is to provide an apparatus for stabilizing a predetermined area of the heart which further comprises a means for anchoring tension or ligation sutures.

The above recited objects of the invention are not intended to so limit the use of the invention. These and other objects of the invention will be apparent to the skilled artisan based upon the following disclosure.

BRIEF DESCRIPTION OF THE DRAWINGS

FIG. 4 is a perspective view showing an alternative embodiment of FIG. 2, in which the stabilizing means comprises a plurality of flexible hooks.

FIG. 5 is a perspective view showing an alternative embodiment of FIG. 2, in which the stabilizing means comprises a plurality of bristles.

FIG. 6 is a perspective view showing an alternative embodiment of FIG. 2, in which the stabilizing means comprises a flexible covering disposed over the second section of the prongs of the bifurcated member.

FIG. 7 is a perspective view showing an alternative embodiment of FIG. 6, in which the flexible covering is a tubular member.

DETAILED DESCRIPTION OF THE INVENTION

The present invention is more particularly described in the following examples which are intended as illustrative only since numerous modifications and variations therein will be apparent to those skilled in the art. As used in the specification and in the claims, "a" can mean one or more, depending upon the context in which it is used.

The present invention, which is shown in FIGS. 1–14, encompasses an apparatus 10 for stabilizing a predetermined area on a heart 2 of a patient to enable a surgical procedure to be performed. The apparatus 10 comprises a bifurcated member 20, an elongated handle segment 40, and a means for joining the handle segment 40 to the bifurcated member 20.

The present invention is ideal for use in heart surgery, in either conventional open heart surgery or in minimally invasive surgery, e.g., minimally invasive coronary artery bypass grafting. One skilled in the art will appreciate, however, that the apparatus of the present invention can be used at any location on or within the body where tissue stabilization or isolation of a predetermined area is desired, including but not limited to the heart, liver kidneys, bladder, stomach, intestines, and vascular and other soft tissue. Thus, the present invention can be used in heart surgery and other soft tissue procedures, such as vascular thrombosis repair, intestinal resection and anastomosis, other intra-abdominal procedures, and the like.

Figure 1:
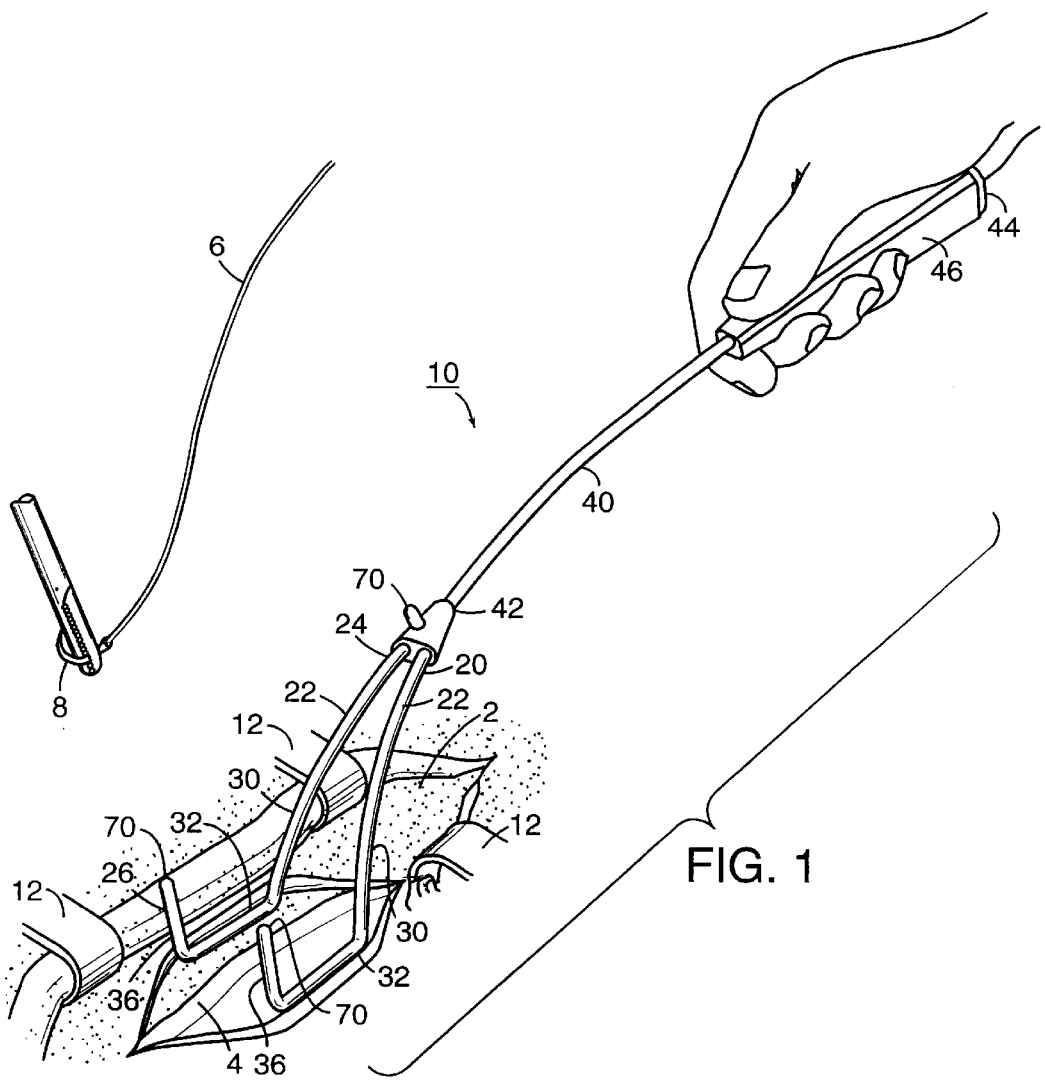
FIG. 1 is a perspective view of one embodiment of the present invention showing the apparatus being placed on the heart of a patient to perform a surgical procedure.

For minimally invasive coronary surgery, access to the heart 2 may be achieved through the ribs of the patient using a rib spreader 12, as shown in FIG. 1. In the typical procedure, the surgeons will usually access the heart 2 via the fourth intercostal space located between the third and fourth ribs, but this may be changed based on the individual patient's anatomy. Since this procedure is sometimes performed on a beating heart 2, it is advantageous to stabilize the heart 2 in the area that the surgical procedure will occur.

The elongated handle segment 40 is used to extend the bifurcated member 20 into the chest of the patient to reach the surface of the heart 2. The handle segment 40 has a first end 42 and an opposite second end 44. As shown in FIG. 1, the handle segment 40 preferably has a hand grip 46 disposed on its second end 44.

Figure 2:
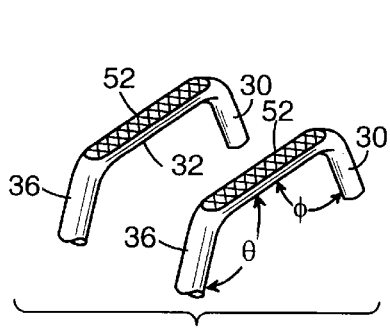
FIG. 2 is a perspective view of one embodiment the stabilizing means of the present invention comprising a textured portion on the second section of the prongs of the bifurcated member.
Figure 3:
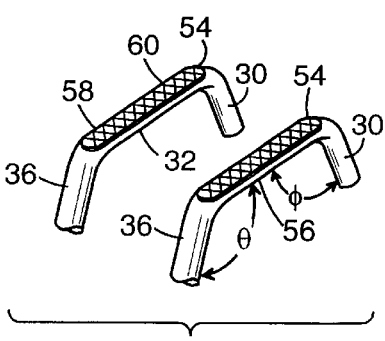
FIG. 3 is a perspective view showing an alternative embodiment of FIG. 2, in which the stabilizing means comprises an insert having a plurality of teeth.

The bifurcated member 20 comprises two elongated prongs 22. Each prong 22 has a proximal end 24 and an opposite distal end 26 and each prong is divided into three sections: a first section 30, a second section 32, and a third section 36. The first section 30 is adjacent the proximal end 24 and terminates in the second section 32. The second section 32 engages the heart 2 and terminates in the third section 36, which is adjacent the distal end 26. It is also preferred that the second sections 32 of each of the two prongs 22 are co-planar, as shown in FIGS. 1–3.

Although including the third section 36 is preferred, it is not necessary in all embodiments. A primary advantage of the third section 36 is that it can be used as a tissue retractor or a retractor to pull a selected item, such as surgical or suture thread 6, away from the area where the surgical procedure is being performed. In addition, the third section 36 can be advantageously positioned to secure suture thread 6 onto a cleat 70 attached to it, which is discussed below.

When the bifurcated member 20 engages the surface of the heart 2 as shown in FIG. 1, the surgeon applies a slight compressive force with the second section 32 on the area that the surgical procedure will occur so that the heart's movement at that specific area is diminished and stabilized. Stabilizing the heart 2 is particularly useful for a heart suturing technique in the area of the coronary arteries, such as the anastomosis of a bypass graft.

It may be advantageous or necessary to compress, block, or otherwise hinder flow in a vein or an artery 4, such as the coronary artery, to perform the surgical procedure. Referring to FIG. 1, one method is placing a traction suture around an artery 4 using a needle 8 and suture thread 6 while the present invention is stabilizing the surface of the heart 2 adjacent to the artery 4. The apparatus 10 can be adapted, as discussed below, to tie off the suture thread 6 onto it.

Figure 13:
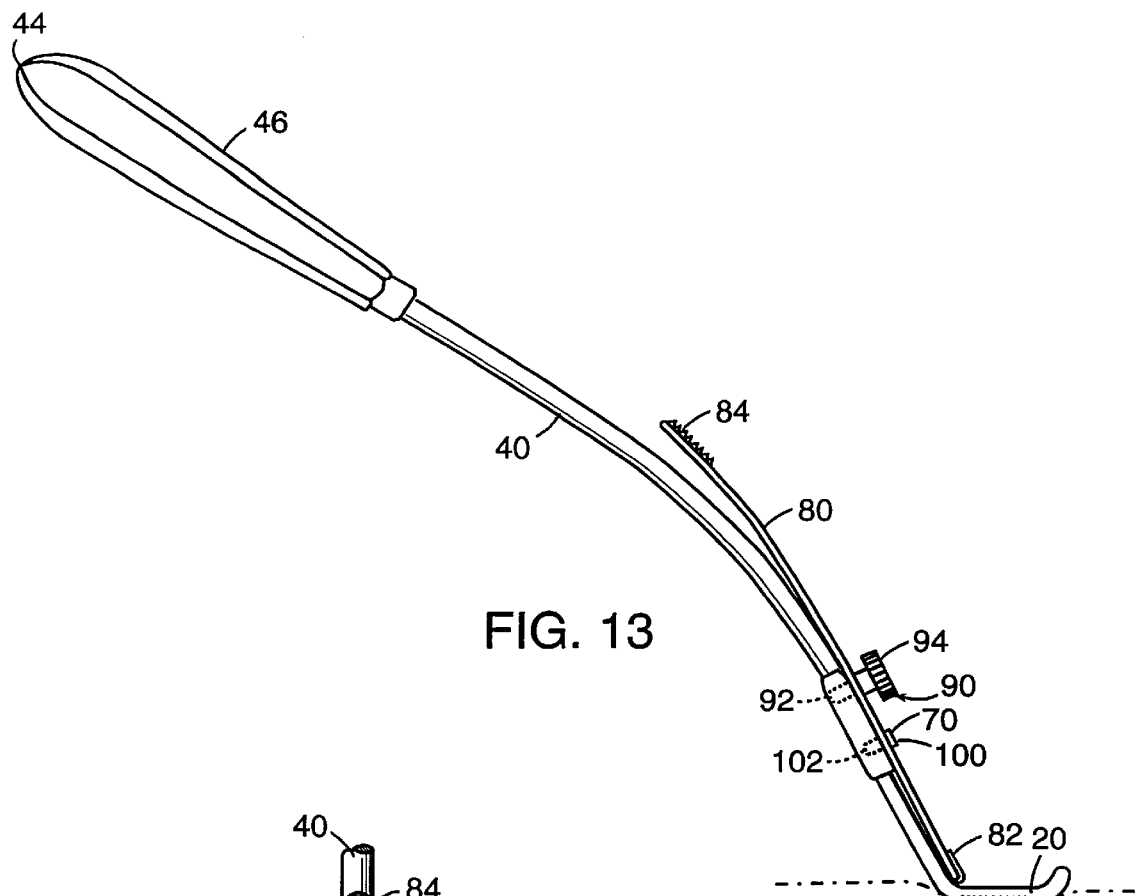
FIG. 13 is a side view of another embodiment of the present invention having an occluding means slidably attached to it.
Figure 14:
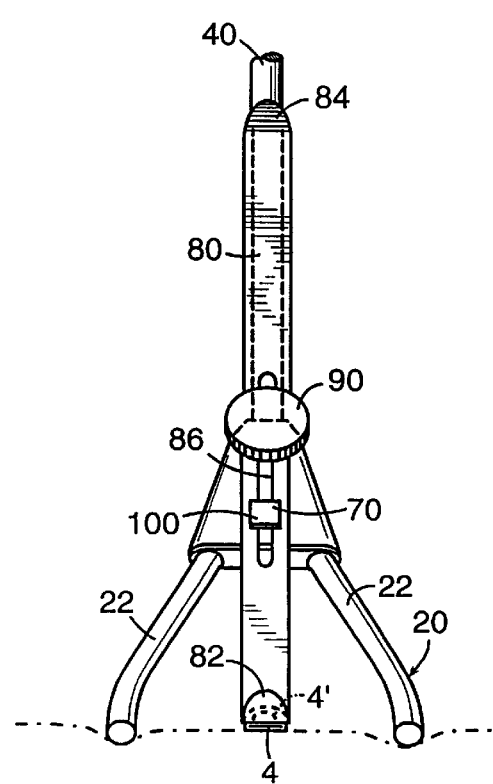
FIG. 14 is a partial front view of FIG. 13 showing the occluding means compressing the coronary artery of the patient.

Another embodiment of the present invention, which can be used in conjunction with or independent of the traction suture, is a means on the apparatus 10 for occluding the artery or vein. The occluding means preferably is movably or slidably coupled to either a portion of the bifurcated member 20 or a portion of the handle segment 40. Referring to FIGS. 13 and 14, the preferred embodiment of the occluding means comprises an elongated occluding member 80 having an engaging end 82 adapted to at least partially compress a portion of the artery 4 and an opposite gripping end 84. The occluding member 80 also defines an elongated slot 86 through a portion of it.

The occluding member 80 is slidably movable between an engaged position and a released position. In the engaged position, which is shown in FIG. 14, the engaging end 82 of the occluding member 80 occludes, or at least partially compresses, the artery 4. The uncompressed cross section of the artery 4 is shown in phantom lines as 4'. In the released position, the occluding member 80 and the artery 4 are spaced apart so that the artery 4 regains its uncompressed shape.

A fastener 90 is disposed through a portion of the slot 86 of the occluding member 80. The fastener 90 has a bottom end 92 adapted to complementarily engage either the bifurcated member 20 or the handle segment 40 and an opposite top end 94. The fastener 90 preferably has a complementarily threaded surface (not shown) with the handle segment 40 or bifurcated member 20 to which it engages.

Rotation of the fastener 90 moves it between a locked and unlocked position, depending on the direction of rotation. In the locked, or tightened, position, a portion of the fastener 90 contacts a portion of the occluding member 80 to frictionally hold the occluding member 80 in either the engaged or released position. In the unlocked position, the occluding member 80 and the portion of the fastener 90 previously contacting the occluding member 80 are spaced apart so that the occluding member 80 is slidably movable between the engaged and release positions. Of course, the fastener 90 and the occluding member 80 do not need to be completely spaced apart to be in the unlocked position, but, instead, sufficiently separated to allow movement therebetween. That is, in the unlocked position, the fastener 90 and the occluding member 80 are adequately physically separated, or disengaged, so that the fastener 90 does not frictionally hold or lock the occluding member 80 in a non-movable position.

The occluding means preferably further comprises a guide member 100 having a lower end 102 fixedly attached to either a portion of the bifurcated member 20 or a portion of the handle segment 40 and a body of a size to be complementarily received within the slot 86 of the occluding member 80. Thus, when the fastener 90 and the body of the guide member 100 are both disposed within the slot 86 and attached to the apparatus 10, the occluding member 80 is only linearly slidable relative to the handle segment 40 and the bifurcated member 20.

For use in heart surgery, the apparatus 10 of the present invention has certain size limitations. For example, the available area to a surgeon to perform a minimally invasive surgical procedure on the heart 2 via an intercostal access is approximately three (3) inches by one and a half (1½) inches. Accordingly, it is desired that width between the second sections 32 be in the range of one half (½) inch to one and a quarter (1¼) inches, more preferably in the range of three quarters (¾) of an inch to one (1) inch. These widths are narrow enough to fit into the confined space, yet wide enough to bridge the area of interest, e.g., bridge the artery 4 that is to be bypassed, as shown in FIG. 1.

Referring back to FIGS. 1–3, the preferred range for the length of the second section 32 is in the range of one half (½) inch to one (1) inch, more preferably in the range of two-thirds (⅔) of an inch to three quarters (¾) of an inch. In the preferred embodiment, each second section 32 is three quarters (¾) of an inch long and separated by three quarters (¾) of an inch from the other second section 32.

The juncture between the first section 30 and the second section 32 forms at least a 90°, or right, angle $\phi$ therebetween. It is preferred that the angle $\phi$ be obtuse so that the surgeon has uninhibited access to the area where the surgical procedure is occurring. An acute angle could be used in the present invention, but it is less desirable because it would likely interfere with the surgical procedure.

Similarly, it is preferred that the juncture between the second section 32 and the third section 36 also form either a right or an obtuse angle $\theta$ therebetween. Although an acute angle is likewise an option, the same problem arises with the interference with the surgical procedure as with angle $\phi$. Also, for certain embodiments, it may be desired to use a different angle $\theta$ for each of the two prongs 22. In the preferred embodiment, however, each prong 22 is substantially "U" shape in side view, which can be appreciated from FIG. 1 and also from FIGS. 2 and 3, which show a truncated inverted "U" shape.

The bifurcated member 20 and the handle segment 40 can be constructed of stainless steel, tantalum, platinum, a memory metal alloy such as nitinol (a nickel/titanium alloy), or other acceptable material for surgical instruments. In one embodiment, the handle segment 40 and/or the prongs 22 are constructed from a malleable nitinol. The nitinol component is normally in the first position (e.g., a rest or memory position) as shown in FIG. 1 when the device is at ambient temperature, e.g., about 23–25° C. Depending upon the surgeon's needs and the specific procedure being preformed, the elongated handle segment 40 or the prongs 22 can be bent and made to assume a second position (not shown) for more effective use of the apparatus during the procedure. For example, use of the memory metal alloy will allow the surgeon to adjust the separation width or angle of any portion of the prongs 22 or the curvature of the handle segment 40.

After completing the surgical procedure, the nitinol component then can be returned to the first, or memory, position by exposing the component to an increased temperature of greater than about 40–65° C., e.g., by autoclaving the instrument after use. Exposing the nitinol to an increased temperature causes the memory metal to expand and straighten so that the any bending or adjustment of the handle segment 40 or the prongs 22 by the surgeon (e.g., movement to the second position) is negated and the nitinol will return to the first position. The apparatus then can be repeatedly used for other surgical procedures over a variety of applications.

As one of skill in the art can appreciate, the memory metal alloy can be used in any selected portion of the apparatus. When used, the diameter of the handle segment 40 constructed of a malleable alloy should be great enough to provide sufficient strength to remain in the second position for use by the surgeon during a procedure. For example, a shaft diameter of greater than about one eighth (⅛) of an inch is preferred for certain procedures. Suitable diameters for the prongs 22 constructed of a memory metal alloy would include diameters greater than about one sixteenth (¹⁄₁₆) of an inch. However, other diameters are also contemplated.

Another aspect of the present invention is a means for stabilizing the second section 32 from sliding on the heart 2 or other organ. The stabilizing means resists sliding or slipping motion between the surface of the heart 2 and the second section 32. The stabilizing means should not be of a type that may potentially damage tissue of the heart 2 or other vital organs with which the apparatus 10 is used.

In one embodiment shown in FIG. 2, the stabilizing means comprises a textured portion 52 on the second section 32. The surface shown in FIG. 2 is a knurled texture. Other embodiments contemplated include a plurality of intersecting slits (not shown) or a DeBakey serrated pattern (not shown) that prevent the second section 32 from sliding when it engages the heart 2.

Referring now to FIG. 3, the stabilizing means can comprise an insert 54 having an attaching surface 56 secured to the second section 32 of each prong 22 and an opposite stabilizing surface 58 which carries the stabilizing means. In FIG. 3, the stabilizing surface 58 of the insert 54 comprises a plurality of tungsten carbide teeth 60. Other materials may be used, however, including stainless steel. As one skilled in the art will appreciate, the teeth should be aggressive enough to prevent sliding, but not so aggressive that they could potentially damage the surface of the heart 2. Now referring to FIG. 4, stabilizing surface 58 of the insert 54 comprises a plurality of flexible hooks 62. The preferred hooks are those of a hook and loop fastener, commonly referred to as VELCRO® fasteners.

Still another embodiment of the stabilizing means is shown in FIG. 5, in which the stabilizing means comprises a plurality of bristles 64. The bristles 64 are disposed at a plurality of different orientations, similar to that of a tube or glass cleaner. Because of the multiple orientations of the bristles 64, any direction that the second section 32 tends to slide is resisted by bristles 64 oriented that direction which resist the motion.

In another embodiment shown in FIG. 6, the stabilizing means comprises a flexible covering 66 disposed over at least a portion of the second section 32. The covering 66 can be a cloth 68, such as cotton, braided cotton, or linen. Other coverings that resist motion when disposed on the surface of a heart 2 can also be used. In another embodiment shown in FIG. 7, the covering 66 is a tubular member 69 selected from the group of silicon, rubber, or plastic. Likewise, other materials that resist motion when disposed on the surface of a heart 2 can also be used. As one skilled in the art will appreciate, other stabilizing means and designs can be used so long as the stabilizing means atraumatically grips the tissue.

Figure 8:
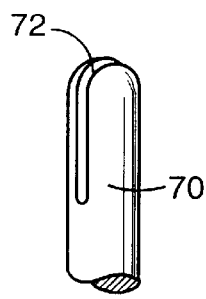
FIG. 8 is an elevated front view of one embodiment of a cleat for use with the present invention.
Figure 9:
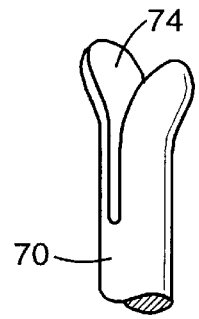
FIG. 9 is an elevated front view showing an alternative embodiment of the cleat shown in FIG. 8.
Figure 10:
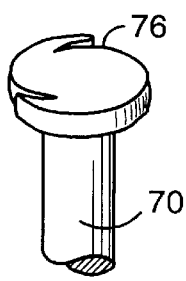
FIG. 10 is an elevated front view showing an alternative embodiment of the cleat shown in FIG. 8.
Figure 11:
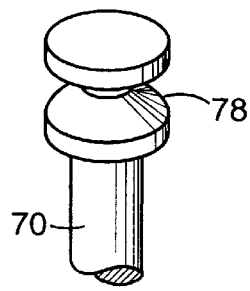
FIG. 11 is an elevated front view showing an alternative embodiment of the cleat shown in FIG. 8.

Another aspect of the present invention is that the apparatus 10 can further comprise a means for securing a portion of a surgical thread 6 used in the surgical procedure. In the preferred embodiment, the securing means comprises at least one cleat 70. Referring back to FIG. 1, the cleat 70 is disposed on the distal end 26 of each of the prongs 22 of the bifurcated member 20. Some of the different embodiments for the cleat 70 are shown in FIGS. 8–11. The preferred embodiment of the cleat 70 that is disposed in the distal end 26 incorporates a slot 72, which is shown in FIG. 8, or a slot with a curved opening 74, which is shown in FIG. 9. Other embodiments that can be placed at the distal end 26 of the prongs 22 include a wedge 76, shown in FIG. 10, or a lateral "V" barrel 78, which is similar in design to a bollard and shown in FIG. 11.

Referring again to FIGS. 1 and 13, it is also preferred to dispose a cleat 70 on either the first end 42 of the handle segment 40 or the proximal end 24 of the bifurcated member 20. More than one cleat 70 can be disposed in this area if the use of the present invention requires multiple cleats 70. Another embodiment disposes a cleat on the guide member 100 of the occluding means. As discussed above and shown in FIGS. 8–11, the cleat 70 can be selected from the group of a wedge 76, a lateral "V" barrel 78, a protrusion having a slot 72 therein, or a protrusion having a slot with a curved opening 74 therein. One skilled in the art will appreciate that other embodiments of the present invention may use other types of cleats 70 and other locations to dispose the cleats 70.

As shown in FIGS. 1 and 13, the joining means, which joins the handle segment 40 to the proximal ends 24 of the two prongs 22, comprises fixedly attaching the first end 42 of the handle segment 40 directly to the proximal end 24 of each of the two prongs 22. Alternatively, the handle segment 40 can be joined to a connecting bar (not shown) disposed so that the connecting bar is fixedly attached to the first end 42 of the handle segment 40 to form a "T" shape. Each end of the connecting bar is also fixedly attached to the proximal end 24 of a respective prong 22 so that the handle segment is fixedly attached to the prongs 22.

Figure 12:
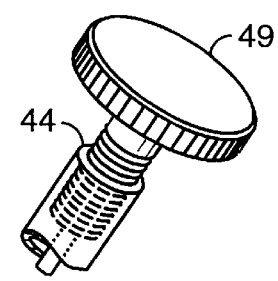
FIG. 12 is a perspective view of another embodiment of the present invention, in which the handle is rotatably and pivotally connected to the bifurcated member.

Another embodiment of the joining means, shown in FIG. 12, is pivotally and rotatably connecting the handle segment 40 to the bifurcated member 20. The preferred embodiment of this joining means comprises a ball and socket, in which a socket 47 is disposed on the first end 42 of the handle segment 40 and a ball 48 is joined to the proximal ends 24 of the two prongs 22 of the bifurcated member 20. The ball 48 is complementarily received within the socket 47.

Preferably, this ball and socket embodiment of the joining means further comprises a means for locking the ball 48 in a selected position within the socket 47 so that the handle segment 40 is disposed at a desired pivotal orientation relative to the second sections 32. Here, the socket 47 is formed of a plurality of individual segments that can be pulled toward each other to lock, or frictionally hold, the ball 48 in the desired position. To pull the segments together, the tightener 49 is rotated, which moves a shaft disposed through a bore of the handle segment 40. The shaft interconnects the socket 47 with the tightener 49, and when the shaft pulls the socket 47 toward the tightener 49, a portion of the socket 47 enters into the first end 42 of the handle segment 40. Thus, the handle segment 40 constricts the size of the socket 47, which causes the segments to be pulled together to securely hold the ball 48.

Other ball and socket embodiments are also contemplated, such as the ball being disposed completely within the bore of the handle segment and the socket being on the lower end of the shaft (not shown). The shaft moves relative to the handle segment between a locked position, in which the socket compress the ball onto the lower end of the bore to hold it in a non-movable position, and an unlocked position.

A hinged connection (not shown) is another joining means contemplated for pivotally connecting the handle segment 40 to the bifurcated member, instead of pivotally and rotatably connecting the components. For this embodiment, the handle segment 40 pivots in a plane that is perpendicular to the plane formed by the second segments 36. Other joining means are also contemplated, such as a swivel mechanism (not shown), similar to a swivel used in fishing. However, as one skilled in the art will appreciate, in some situations it may be preferred to use a joining means that both rotatably and pivotally connects the bifurcated member 20 to the handle segment 40 that can lock the bifurcated member 20 when disposed on the heart 2 in a desired position relative to the handle segment 40. In other cases such as when the occluding means is used with the apparatus 10, fixedly attaching the first end 42 of the handle segment 40 to the proximate end 24 of the two prongs 22 is desired.

One advantage of the joining means rotatably or pivotally connecting the handle segment 40 and bifurcated member 20 is that these components can be pre-aligned so that the bifurcated member 20 is self-positioning on the patient's heart 2 by lowering the handle segment 40. Once the surgeon lowers the bifurcated member 20 to the desired position, the surgeon can then maintain the second sections 32 engaging the heart 2 while re-orienting the handle segment 40, if required, to a position that allows the greatest access to the surgery site. When the handle segment 40 is at the desired orientation, the assembly is tightened, preferably by a single turn of the tightening portion 49, to secure the handle segment 40 at a desired position. An undesirable alternative is to have another surgeon or nurse hold the handle segment 40 during the surgical procedure, which creates problems with space constraints, fluctuations in the pressure that the second sections 32 placed on the heart 2, and increased costs for the extra person to hold the handle segment 40.

Also, the joining means can further comprise a means for removably, or interchangeably, mounting the bifurcated member 20 to the handle segment 40. The bifurcated member 20 thus can be detachably secured to the handle segment 40 and is interchangeable with another bifurcated member 20, e.g., a bifurcated member in which the prongs are a different size or have a different separation distance therebetween. An example is separating the segments of the socket 47 shown in FIG. 12 to remove the ball 48 and attached bifurcated member 20 and installing a different ball and bifurcated member.

Another aspect of the present invention is a means for attaching the handle segment 40 to a rib spreader 12 (shown in FIG. 1) or other similar equipment (not shown) that remains stationarily positioned on or adjacent to the patient during the surgical procedure. That is, since access to the heart 2 may be achieved using a rib spreader 12, it is desired to have a means to hold the apparatus 10 at the desired stationary position. A swivel head attachment 14 (shown in FIG. 12) coupled to the rib retractor 12, can serve this purpose. Since the assembly 14 is adapted to pivotally and slidably engage a portion of the rib retractor 12, the handle segment 40 and attached bifurcated member 20 can move relative to the retractor 12 to an optimal position. As one skilled in the art will appreciate, there are other devices available to attach the handle segment 40, such as the ball and socket connection (not shown), so that the second section 32 is maintained at a desired position without a person physically holding the handle segment 40.

Although the present invention has been described with reference to specific details of certain embodiments thereof, it is not intended that such details should be regarded as limitations upon the scope of the invention except as and to the extent that they are included in the accompanying claims.

What is claimed is:

1. An apparatus for stabilizing a predetermined area on a heart of a patient to enable a surgical procedure, comprising:
   a. a bifurcated member having two elongated prongs, each prong having a proximal end and an opposite distal end, said prongs attached to each other adjacent the proximal ends thereof, at least a portion of each prong adapted to enrage the heart of the patient;
   b. an elongated handle segment having a first end and an opposite second end;
   c. means for joining the first end of said handle segment to said bifurcated member adjacent the proximal end thereof; and
   d. means for occluding an artery of the patient, wherein said occluding means is moveably coupled to a portion of said handle segment, and wherein said occluding means comprises:
      i. an elongated occluding member having an engaging end adapted to at least partially compress a portion of the artery of the patient, said occluding member defining an elongated slot through a portion thereof;
      ii. a fastener having a top end and an opposite bottom end extending therefrom to be complementarily received within the slot of said occluding member, wherein a portion of the bottom end of said fastener operatively engages a portion of said handle segment adjacent the first end of said handle segment; and
      iii. a guide member having a lower end fixedly attached to said handle segment and a body section to be complementarily received within the slot of said occluding member, wherein, when a portion of the bottom end of said fastener and a portion of the body section of said guide member are disposed within the slot, said occluding member is only linearly slidable relative to said handle segment and said bifurcated member.

2. An apparatus for stabilizing a predetermined area on a heart of a patient to enable a surgical procedure, comprising:
   a. a bifurcated member having two elongated prongs, each prong having a proximal end and an opposite distal end, said prongs attached to each other adjacent the proximal ends thereof, at least a portion of each prong adapted to engage the heart of the patient;
   b. an elongated handle segment having a first end and an opposite second end;
   c. means for joining the first end of said handle segment to said bifurcated member adjacent the proximal end thereof; and
   d. means of occluding an artery of the patient, wherein said occluding means is moveably coupled to a portion of said bifurcated member, and wherein said occluding means comprises:
      i. an elongated occluding member having an engaging end adapted to at least partially compress a portion of the artery of the patient, said occluding member defining an elongated slot through a portion thereof;
      ii. a fastener having a top end and an opposite bottom end extending therefrom to be complementarily received within the slot of said occluding member, wherein a portion the bottom end of said fastener operatively engages a portion of said bifurcated member adjacent the proximal ends of said prongs; and
      iii. a guide member having a lower end fixedly attached to a portion of said bifurcated member and a body section of a size to be complementarily received within the slot of said occluding member, wherein, when a portion of the bottom end of said fastener and a portion of the body section of said guide member are disposed within the slot, said occluding member is only linearly slidable relative to said handle segment and said bifurcated member.

3. An apparatus for stabilizing a predetermined area on a heart of a patient, the apparatus comprising:
   a. a stabilizing device having a first surface sized to contact the predetermined area of the heart of the patient and a second surface thereon;
   b. an elongated handle segment having a first end and an opposite second end;
   c. a connecting member for connecting said stabilizing device to said handle segment, wherein said connecting member connects the first end of said elongated handle segment to the second surface of said stabilizing device;
   d. an occluding member which is moveably coupled to said handle segment and is movable linearly relative to said handle segment between a released position and an engaged position;
   e. wherein the first surface of said stabilizer device includes a plurality of spaced apart and generally co-planar stabilizing members thereon and
      wherein at least a portion of said occluding member is generally adjacent to and positioned between two of the plurality of spaced apart and generally co-planar stabilizing members of the first surface in the engaged position.

4. The apparatus of claim 3, wherein said occluding member includes an engaging end thereon, and wherein the engaging end is generally spaced apart from the second surface of said stabilizing device in the released position.

5. The apparatus of claim 3, wherein the first surface of said stabilizer device includes a plurality of spaced apart and generally co-planar stabilizing members thereon, wherein said occluding member includes an engaging end thereon, and wherein the engaging end extends generally beyond the plurality of spaced apart and generally co-planar stabilizing members of said stabilizing device in the engaged position.

6. An apparatus for stabilizing a predetermined area of a heart of a patient, the apparatus comprising:
   a. a stabilizing device having a first surface sized to contact the predetermined area of the heart of the patient and a second surface thereon;
   b. an elongated handle segment having a first end and an opposite second end;
   c. a connecting member for connecting said stabilizing device to said handle segment, wherein said connecting member connects the first end of said elongated handle segment to the second surface of said stabilizing device;
   d. an occluding member which is moveably coupled to said stabilizing device and is movable linearly relative to said handle segment between a released position and an engaged position; and
   e. wherein the first surface of said stabilizer device includes a plurality of spaced apart and generally co-planar stabilizing members thereon, and wherein at least a portion of said occluding member is generally adjacent to and positioned between two of the plurality of spaced apart and generally co-planar stabilizing members of the first surface in the engaged position.

7. The apparatus of claim 6, wherein said occluding member includes an engaging end thereon, and wherein the engaging end is generally spaced apart from the second surface of said stabilizing device in the released position.

* * * * *

UNITED STATES PATENT AND TRADEMARK OFFICE
CERTIFICATE OF CORRECTION

PATENT NO : 6,071,235
DATED : June 6, 2000
INVENTOR(S) : Gregory R. Furnish and Christopher S. Looney It is certified that error appears in the above-identified patent and that said Letters Patent are hereby corrected as shown below:

Title page,

Page 2, col. 1, under "OTHER PUBLICATIONS", "Mini-Sternotomy for Coronary Artery...", replace "oif Thorac" with --of Thoracic--;

Page 2, col. 2, under "OTHER PUBLICATIONS", "Surgical Management of Diseased...", replace "M" with --MD--;

Page 2, col. 2, under "OTHER PUBLICATIONS", "Technique of Internal Mammary...", replace "78:45 79" with --78:455-479--;

Col. 2, line 22, replace "surge on" with --surgeon--;

Col. 10, claim 1, line 41, replace "enrage" with --engage--.

Signed and Sealed this

First Day of May, 2001

*Attest:*

NICHOLAS P. GODICI

*Attesting Officer*  *Acting Director of the United States Patent and Trademark Office*